United States Patent
Dingley

(10) Patent No.: US 9,138,551 B2
(45) Date of Patent: Sep. 22, 2015

(54) VENTILATOR APPARATUS

(75) Inventor: John Dingley, Swansea (GB)

(73) Assignee: ART OF XEN LIMITED, Cardiff (GB)

( * ) Notice: Subject to any disclaimer, the term of this patent is extended or adjusted under 35 U.S.C. 154(b) by 710 days.

(21) Appl. No.: 13/322,143

(22) PCT Filed: May 19, 2010

(86) PCT No.: PCT/GB2010/001009
§ 371 (c)(1),
(2), (4) Date: Jan. 17, 2012

(87) PCT Pub. No.: WO2010/133843
PCT Pub. Date: Nov. 25, 2010

(65) Prior Publication Data
US 2012/0103333 A1 May 3, 2012

(30) Foreign Application Priority Data

May 19, 2009 (GB) .................................. 0908523.4

(51) Int. Cl.
*A61M 16/08* (2006.01)
*A61M 16/20* (2006.01)
(Continued)

(52) U.S. Cl.
CPC ........... *A61M 16/00* (2013.01); *A61M 16/0081* (2014.02); *A61M 16/20* (2013.01); *A61M 16/0078* (2013.01); *A61M 16/08* (2013.01); *A61M 16/22* (2013.01)

(58) Field of Classification Search
CPC ............ A61M 16/00; A61M 16/0045; A61M 16/0081; A61M 16/01; A61M 16/1015; A61M 16/20; A61M 16/0833; A61M 16/08; A61M 16/0051; A61M 16/206; A61M 16/0096; A61M 16/10; A61M 16/104; A61M 16/12; A62B 7/00; A62B 7/02; F15B 3/00; F16L 55/04; F16L 55/052
USPC ............. 128/200.24, 204.28, 205.13–205.17, 128/203.12, 203.28, 204.18, 204.21, 128/204.23, 204.25, 205.12, 205.14, 128/205.15, 898
See application file for complete search history.

(56) References Cited

U.S. PATENT DOCUMENTS 3,741,250 A * 6/1973 Mercier .......................... 138/30
3,831,595 A * 8/1974 Valenta et al. ........... 128/202.22
(Continued)

FOREIGN PATENT DOCUMENTS

EP 0830166 1/2000
FR 2806919 10/2001
(Continued)

OTHER PUBLICATIONS

British Search Report dated Sep. 7, 2009 for related British Patent Application No. GB09808523.4.
(Continued)

*Primary Examiner* — Annette Dixon
(74) *Attorney, Agent, or Firm* — Troutman Sanders LLP; Ryan A. Schneider; Benjamin C. Wiles

(57) ABSTRACT

Ventilator apparatus provides a breathing circuit for supplying breathing gas to a patient. The breathing circuit includes a variable volume enclosure (3) provided within an enclosure chamber (2) and a gas supply path (21) into the enclosure chamber enabling the enclosure chamber to be pressurized by the supplied gas in order to vary the volume of the enclosure. An alternative path (9) for the gas supply is provided enabling the gas supplied, in predetermined circumstances, to enter directly into the breathing circuit via a valve (4). The gas supply path into the chamber is directed such that as a result of gas passing into the enclosure chamber the valve is biased more firmly to a closed condition.

16 Claims, 9 Drawing Sheets

Time Axis.
Start of Inspiration    End of Inspiration

(51) Int. Cl.
*A61M 16/22* (2006.01)
*A61M 16/00* (2006.01)

(56) References Cited

U.S. PATENT DOCUMENTS

| | | | | |
|---|---|---|---|---|
| 4,256,100 A | * | 3/1981 | Levy et al. | 128/204.21 |
| 4,821,712 A | * | 4/1989 | Gossett | 128/205.15 |
| 5,490,499 A | * | 2/1996 | Heinonen et al. | 128/203.28 |
| 5,857,458 A | | 1/1999 | Tham et al. | |

FOREIGN PATENT DOCUMENTS

| | | |
|---|---|---|
| WO | 9641651 | 12/1996 |
| WO | 9962581 | 12/1999 |
| WO | 2004064907 | 8/2004 |

OTHER PUBLICATIONS

International Search Report dated Nov. 12, 2010 for related PCT Application No. PCT/GB2010/001009.

* cited by examiner

VENTILATOR APPARATUS

CROSS-REFERENCE TO RELATED APPLICATIONS

This application is a US National Stage of International Application No. PCT/GB2010/001009, filed 19 May 2010, which claims the benefit of 0908523.4, filed 19 May 2009, both herein fully incorporated by reference.

FIELD OF THE INVENTION

The present invention relates to ventilator apparatus and particularly to such apparatus used for patient breathing applications.

BACKGROUND OF THE INVENTION

Ventilator apparatus for use in patient care applications is disclosed in, for example EP0830166. The system disclosed includes a 'bag in bottle' ventilation system which consists of a bellows provided in a transparent sealed container. This disclosed "bag in bottle" arrangement is intended to be connected to a patient breathing circuit which can be of several standard conventional designs but must include a carbon dioxide scrubbing component such as a container of "sodalime" as might commonly be used in anaesthesia breathing systems for example. The bellows (and the rest of the chosen breathing circuit to which it is attached) contains either oxygen or a breathing gas mixture which includes enough oxygen to sustain life—typically 21% oxygen or greater (as normal air comprises 21% oxygen).

The container is provided with an inlet enabling a ventilator device to deliver oxygen into the container in a cyclic fashion as a "driving gas" to compress the bellows, so ventilating the lungs via the breathing circuit to which the bellows are attached. The bellows has a one way valve that can open to permit a small portion of "driving gas" oxygen to enter the interior of the bellows (and breathing circuit to which the bellows are attached) but this only occurs when the bellows has lowered successively during successive inhalation/exhalation cycles to abut the 'bump stops' at the base of the container. When this occurs the pressure outside the bellows becomes greater than the pressure within it by an amount sufficient to open the one way valve of the bellows. This allows a small portion of the "driving gas" oxygen pumped from the ventilator to pass into the bellows to automatically replace the oxygen therein, according to the needs of the patient. The arrangement of EP0830166 can be used for delivery of anaesthetic to a patient. An advantage of such an arrangement is that it automatically tops itself up with oxygen to replace oxygen metabolically taken up by the patient from their lungs into their blood, during breathing. No anaesthetic gas that has additionally been added to the breathing circuit (to which the bellows is connected) is permitted to escape from the closed loop system. This is beneficial where expensive anaesthetics are used for example Xenon gas, as in this manner, the only loss of anaesthetic gas or vapour from the breathing system is by patient tissue uptake via their lungs. The design becomes particularly cost-efficient as a delivery system with vapors or gases which are taken up only very slowly by the patient, particularly if they are expensive. Xenon is a prime example of a gas which exemplifies both these conditions, while sevoflurane would be an example of an anaesthetic vapour which fulfils these conditions. As disclosed in EP0830166, alternative valve arrangements may be used to top up the oxygen into the closed loop system. Also the bellows can be replaced with other arrangements such as an inflatable rubber bag or similar.

For a system operating efficiently, it is important that 'top up' oxygen is permitted to pass into the system only at the end of inspiration via the valve which can be thought of as an "oxygen substitution valve." A problem with prior art arrangements is that due to inherent constraints in known one way valves, the valve may open or flutter during the inspiratory phase, allowing oxygen to leak in prematurely. If this flutter and premature leakage is very minor then the effect will be negligible, as any residual requirement to replace oxygen is completed when the bellows or bag empties, by the correct operation of the valve at the end of the inspiration phase.

However, if the valve flutter and oxygen leakage into the breathing circuit is excessive, more oxygen can end up being added than was consumed during the previous breath cycle, resulting in the bellows or bag filling and becoming more distended at each end expiration. In other words excessive oxygen is added over time, in excess of the patient uptake. By adding oxygen at a rate matching uptake (correct operation), the gas mixture in the breathing circuit stays constant or only changes slowly over time—this is advantageous for the physician running the anaesthetic procedure for example. If oxygen is added at a rate exceeding patient uptake, the bellows will eventually completely fill and any excess volume is thereafter vented from the circuit via standard conventional safety valves (not shown) present in all such anaesthesia and similar systems to prevent pressure build-up and lung damage. If the circuit "vents" excess gases in this way, it will still function as a mechanical ventilation circuit but any advantages in terms of gas economy offered by its totally closed recirculating nature are then lost. If the patient is a newborn baby, a situation where oxygen is being added (in gross excess of patient uptake) is risky to the health of the baby as an excessively high oxygen concentration in the breathing gas mixture (that would result) can be harmful, for example causing blindness. Where the patient is physically small (for example for a baby) and the oxygen consumption rate is very low in absolute terms, the margin of "error" with respect to correct function of the oxygen substitution valve (opening at end-inspiration only) is very small. In this situation even a small degree of premature valve "flutter" and oxygen addition during the inspiration phase, rather than at end-inspiration, could very easily lead to more oxygen being added than was consumed during the previous breathing cycle. In such a situation, premature opening of the valve is dangerous and unacceptable because too much oxygen will be added over time to the recirculating part of the system.

FIG. 1 shows an exemplary system that will be likely to suffer from the problem described. A mechanical ventilator 101 pumps oxygen into the chamber 102. An inflatable rubber bag 103 is positioned internally of the chamber and is collapsed and expanded during the breathing cycle. A disc valve 104 (the oxygen substitution valve) normally rests in a closed position but when the pressure differential above and below the valve is sufficient the disc valve is caused to be raised to an open position permitting top up oxygen to be delivered to the system. This should only happen at the end of the inspiratory phase in a correctly operating system. The system loop shown includes an integrated carbon dioxide absorber 106 containing for example, soda lime granules.

However, in actual operation, as the mechanical ventilator 101 pumps oxygen, it takes a moment for the pressure in the chamber 102 to be transmitted to the interior of the inflatable rubber bag 103. Consequently it takes a moment for the gas pressure above the disc valve 104 to equalize with the gas pressure below the disc valve 104. Therefore the valve may open or flutter during the inspiratory phase, allowing oxygen to leak into the upper chamber 105 and pass into the closed system prematurely. A crude solution is to spring load the disc valve 104 in order to require more force to open the valve 104. The mechanical energy required to open such a spring loaded valve at the end of inspiration would be provided by the ventilator not the patient so on the face of it this may appear to be acceptable. However such an arrangement is unsatisfactory as it interferes with operation of the ventilator machine by causing an (abnormal) pressure spike in the recorded pressure at the mechanical ventilator.

FIG. 2 shows a pressure vs. time recorded plot for a ventilator without a spring loaded valve (but with a valve prone to the flutter problem). The plot is for the inspiration phase and measures not the pressure in the lungs but the pressure at the point where the mechanical ventilator attaches to the lower chamber 102 (i.e. the pressure in the lower chamber 102). In this plot the opening pressure of the disc valve is minimal (the disc valve is not spring loaded). The valve opens at the end of inspiration (point A) without requiring a rise in pressure generated by the mechanical ventilator in order to open the valve.

FIG. 3 shows a plot similar to FIG. 3, but this time for a disc valve which has been spring loaded to prevent flutter during the inspiration phase. The valve opens at the end of inspiration (point A) but in this instance requires a rise in pressure generated by the mechanical ventilator in order to open the valve. This rise in required opening pressure can be seen as the step at point A. As a result the pressure/time waveform is abnormal. Although not necessarily harmful to a patient certain advanced mechanical ventilators may interpret this abnormality as for example a patient coughing against the ventilator and activate a warning alarm as a result. Such a step increase in the required opening pressure is also undesirable as the peak pressure apparently being delivered to the lungs from the display appears to be 22 cmH2O when in reality it is less than this.

BRIEF SUMMARY OF THE INVENTION

Accordingly it has been determined that a non spring loaded lightweight valve that does not flutter is a preferred engineering solution to this problem.

An improved arrangement has now been devised.

According to a first aspect, the present invention provides ventilator apparatus comprising a breathing circuit for supplying breathing gas to a patient, the breathing circuit including a variable volume enclosure provided within an enclosure chamber; a gas supply path into the enclosure chamber being provided, permitting the enclosure chamber to be pressurised by the supplied gas in order to vary the volume of the variable volume enclosure; an alternative path for the gas supply being provided enabling the gas supplied, in predetermined circumstances, to enter directly into the breathing circuit via valve means (the oxygen substitution valve); the gas supply path into the chamber being directed such that as a result of gas passing into the enclosure chamber the valve means is biased more firmly to a closed condition.

It is preferred that the gas supply path into the enclosure chamber is directed such that as a result of gas passing into the chamber, the enclosure chamber-side pressure at the valve means becomes reduced. This may be achieved by entraining gas to flow in a direction away from the valve means thereby reducing the chamber-side pressure at the valve means. A venturi (or venturi like) arrangement may beneficially be used.

Beneficially, the enclosure chamber-side pressure at the valve means becomes reduced slightly and with respect to the breathing circuit-side pressure. The effect to urge the valve means more firmly to a closed condition is beneficially tailored to occur temporarily at the beginning of the inspiration phase of the breathing cycle.

In one realisation of the invention, the gas supply is directed into the chamber away from a conduit connection to the valve means. A baffle or deflector may be provided at the enclosure chamber to direct the supply gas away from the valve and/or toward the variable volume enclosure.

Alternatively, a gas supply conduit may be used, having an outlet end communicating with the chamber, the gas supply conduit extending past conduit connection to the valve means.

Beneficially the valve means comprises a valve element (such as a valve disc) arranged to rest on a valve seat in a valve closed configuration. Beneficially the weight of the valve disc is sufficient to hold it in place in the closed configuration. Ideally, with the described improvements, the valve can be of low mass and still remain seated until end-inspiration. The valve element is arranged to lift from the valve seat in the valve open configuration. A cage or other enclosure may be provided to hold the valve element captive.

It is preferred that the valve means is arranged to open when the variable volume enclosure is in a maximum collapsed state. Opening is beneficially as a result of pressure differential on opposed sides of the valve means.

In one embodiment, the variable volume enclosure comprises a flexible bag or pouch.

In an alternative embodiment, the variable volume enclosure comprises a collapsible bellows arrangement.

The apparatus of the invention is particularly suitable for delivering anaesthetic to a patient.

In an embodiment in which the variable volume enclosure comprises a flexible bag or pouch, it may be preferred that the wall of the enclosure chamber includes a concave form surface arranged to nest or cradle, i.e. conform to the shape of, adjacent portions of the flexible bag or pouch in its expanded state. This minimises the 'dead volume' in the enclosure chamber.

This is believed to be novel and inventive per se. accordingly, a second aspect of the invention provides ventilator apparatus comprising a breathing circuit for supplying breathing gas to a patient, the breathing circuit including a variable volume flexible bag or pouch provided internally of an enclosure chamber; a gas supply path into the enclosure chamber being provided, permitting the enclosure chamber to be pressurised by the supplied gas in order to vary the volume of the bag or pouch; wherein the wall of the enclosure chamber includes a concave form surface arranged to nest or cradle, i.e. conform to, adjacent portions of the flexible bag or pouch in its expanded state.

BRIEF DESCRIPTION OF THE DRAWINGS

The invention will now be further described in specific embodiments by way of example only and with reference to the accompanying drawings.

DETAILED DESCRIPTION OF PREFERRED EMBODIMENTS

Figure 1:
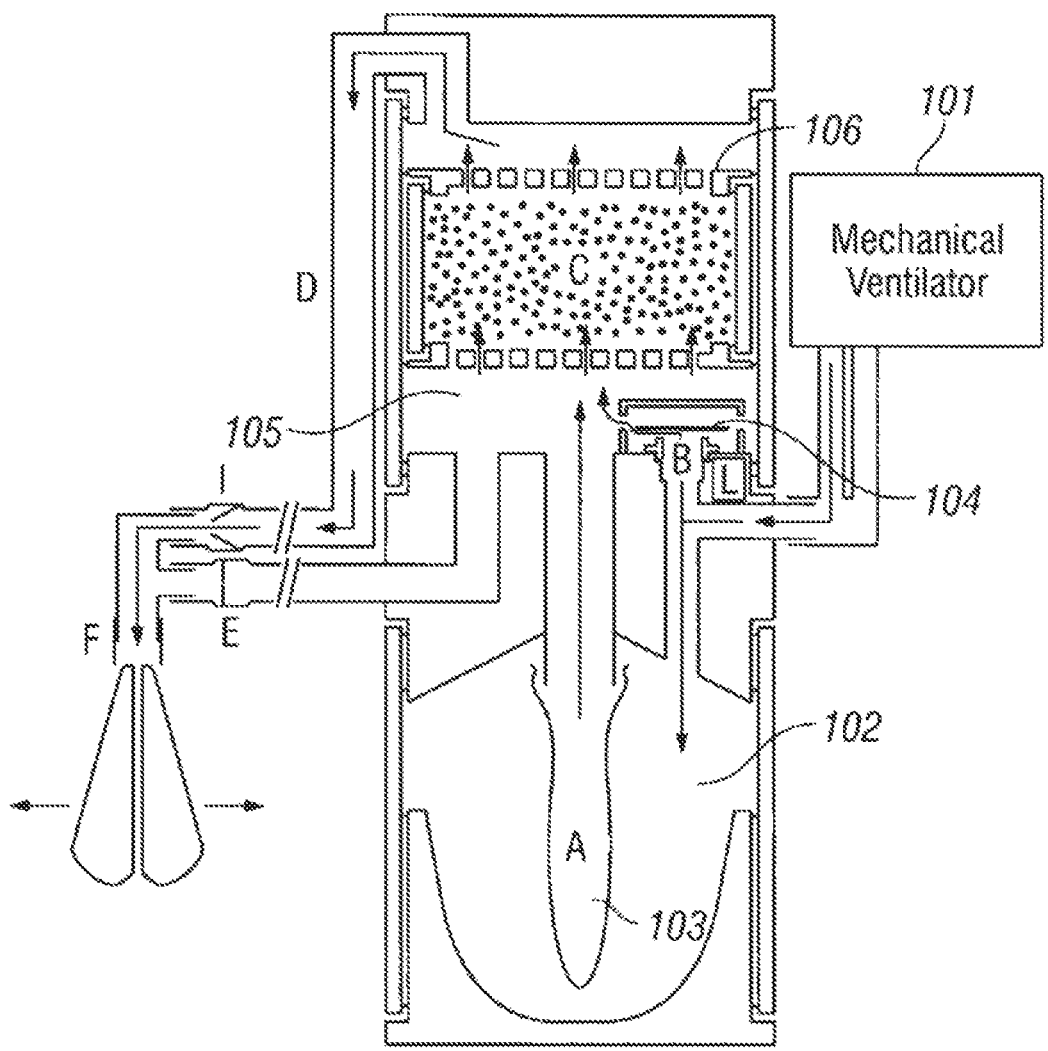
FIG. 1 is a schematic view of ventilator apparatus described in relation to problems to be overcome by the invention.
Figure 2:
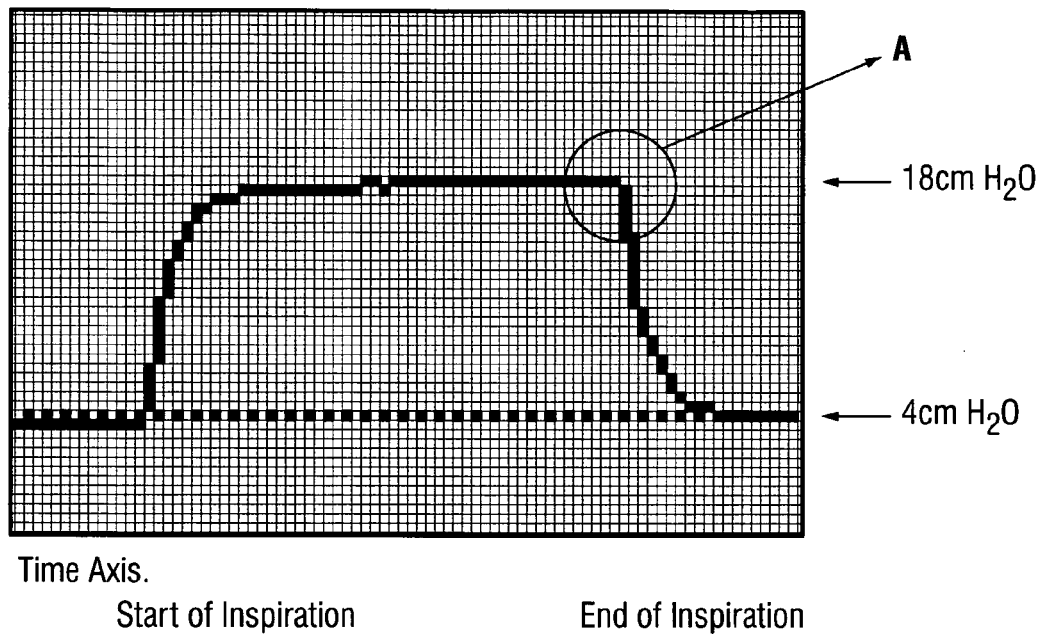
FIG. 2 is a pressure versus time plot for a ventilator machine having a non-spring loaded disc valve.
Figure 3:
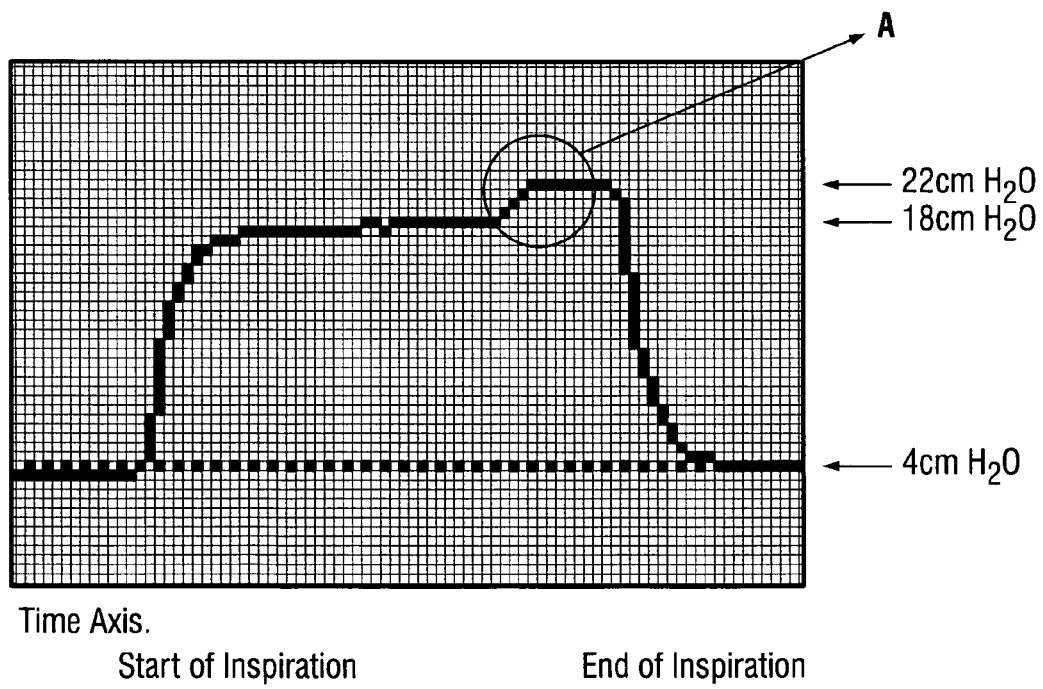
FIG. 3 is a pressure versus time plot for a ventilator machine having a spring loaded disc valve.
Figure 4:
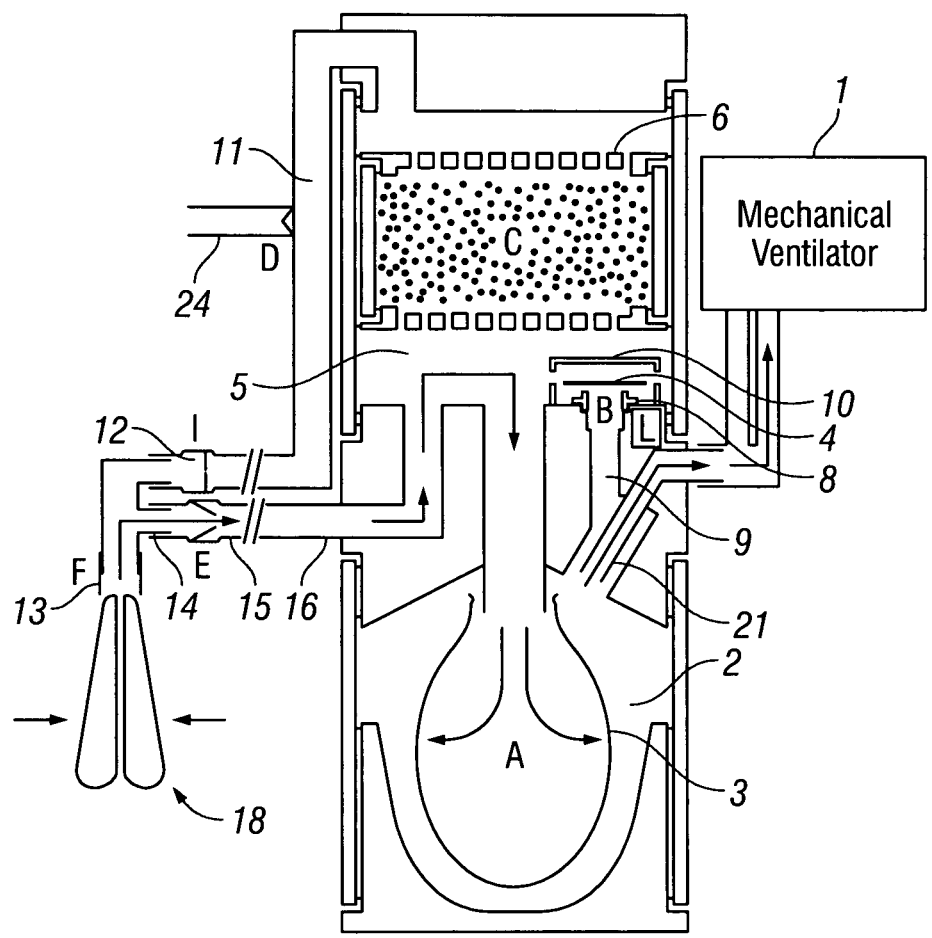
FIG. 4 is a schematic representation of a first embodiment of ventilator apparatus in accordance with the invention in the expiratory phase.
Figure 5:
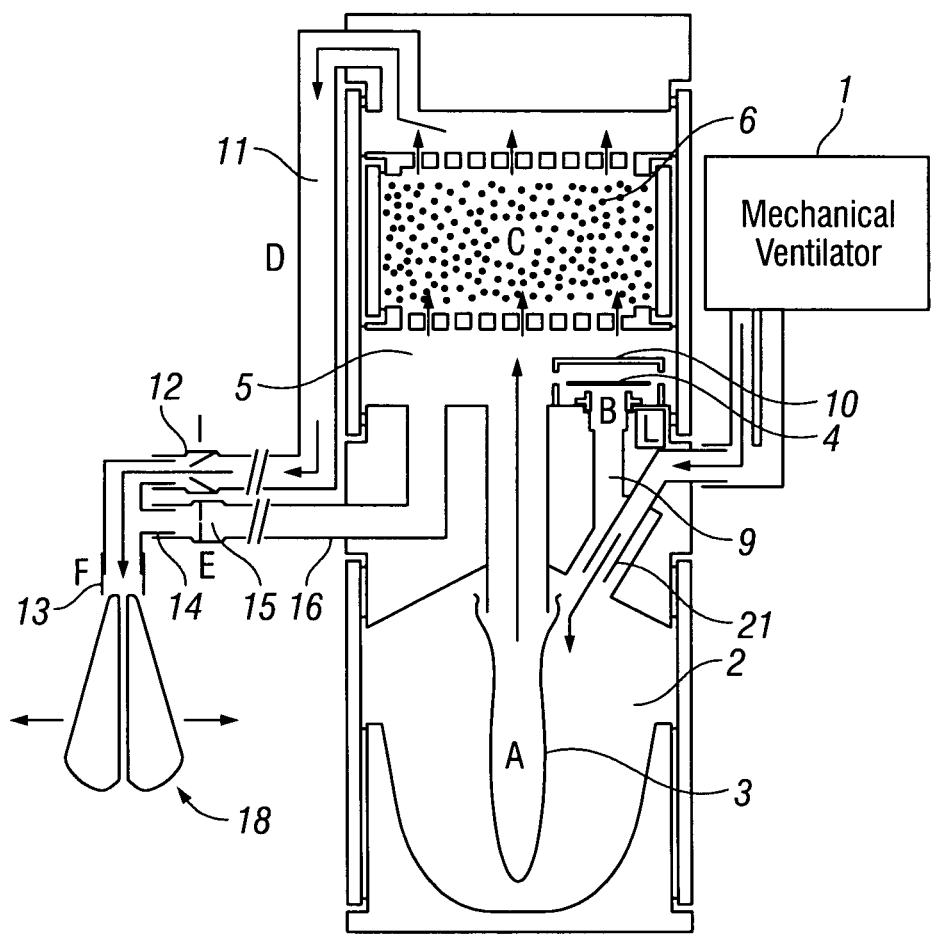
FIG. 5 is a schematic representation of the first embodiment of ventilator apparatus part way through the inspiratory phase.
Figure 6:
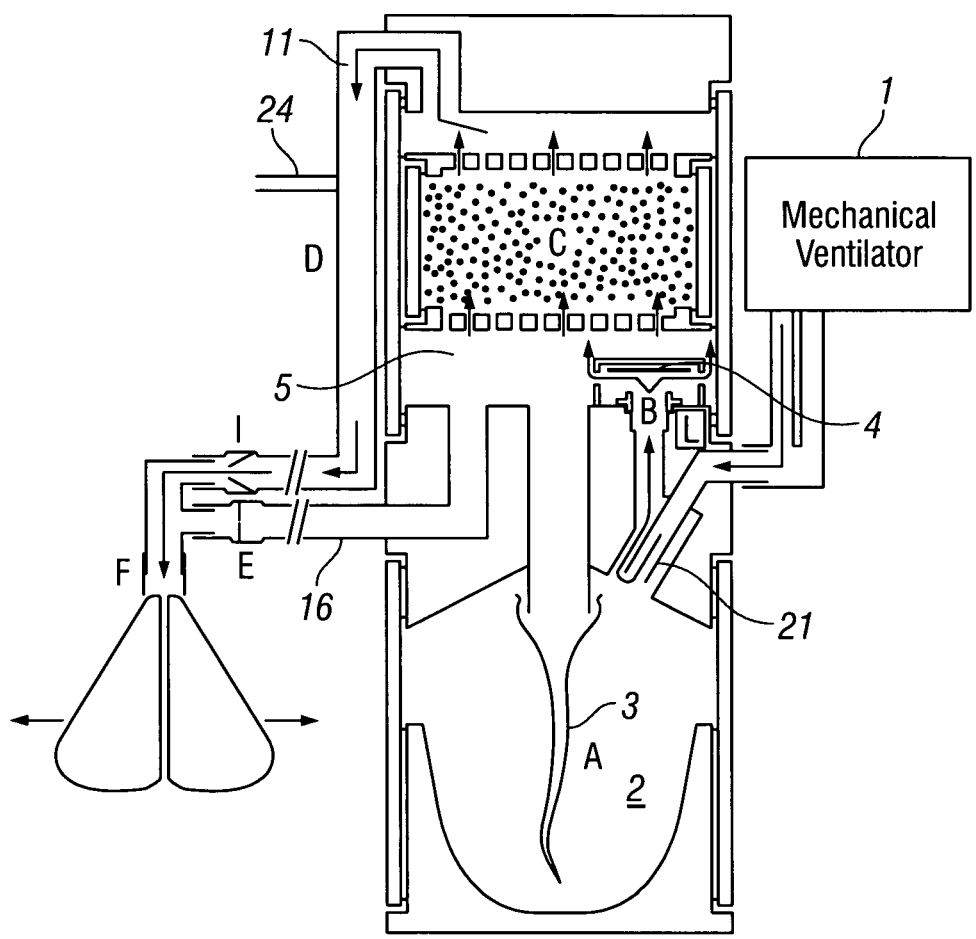
FIG. 6 is a schematic representation of the first embodiment of ventilator at the end of the inspiratory phase.

Referring to the drawings, and initially to FIGS. 4 to 6, the ventilator apparatus is generally similar in aspects to the arrangement of FIG. 1 and comprises a mechanical ventilator machine 1 which pumps oxygen into the chamber 2. An inflatable rubber bag 3 is positioned internally of the chamber and is collapsed and expanded during the breathing cycle. A disc valve 4 normally rests in a closed position on a valve seat 8 at the top of a conduit 9 communicating between the upper chamber 5 and the bag chamber 2. The valve disc 4 is retained in a cage 10 which permits the valve to be lifted from seat 8 when the pressure differential above and below the valve disc 4 is sufficient. In such circumstances the disc valve 4 (the oxygen substitution valve) is caused to be raised to an open position permitting top up oxygen to be delivered to the system. The system loop includes a carbon dioxide absorber 6 containing soda lime granules. In this embodiment it is advantageously and conveniently formed as part of the whole structure (to facilitate possible manufacture of the lower container, bag in bottle, oxygen substitution valve, and soda-lime chamber enclosures as one integrated design) but could functionally be placed at a different position within the recirculating gas loop (recirculating gas loop is the upper part of the machine in this embodiment, soda-lime container and the hoses to/from patient with unidirectional valves). A communication conduit 11 delivers oxygen via a one way valve 12 to a patient breathing connection 13. A return conduit 14 communicates with the breathing connection 13 and communicates via a one way valve 15 and return conduit 16 with the interior of the inflatable bag 3. The patient's lungs are shown schematically at 18.

The mechanical ventilator machine pumps oxygen via the conduit 21 into the bag chamber 2 to instigate the inspiration cycle. Conversely during the expiration phase, the oxygen in the chamber 2 vents to atmosphere via the ventilator machine 1.

In use, initially the system is primed by filling with oxygen or an oxygen containing mixture. The breathing connection is connected to the patient (for example to an endotracheal tube positioned in the trachea of a patient) and secured. The ventilator machine alternately pumps oxygen into the chamber 2 via the conduit 21, and then vents to atmosphere. Thus on each cycle, oxygen enters the chamber 2 via conduit 21 increasing the pressure in the chamber 2 and pressing in on the wall of the bag 3 tending to collapse the bag 3. The oxygen containing gas within the bag 3 is accordingly driven into the closed loop breathing circuit towards the patient connector 13 via the conduit 11 and one way valve 12. The patients lungs are then filled with gas causing them to expand. As the mechanical ventilator cycles to the expiratory phase of the ventilation cycle, exhaled gas containing carbon dioxide is then exhaled from the lungs 18 due to the passive recoil of the chest of the patient and these pass back into the circuit via the connector 13. The gases then pass via the one way valve 15 and conduit 16 into the interior of the bag 3. The carbon dioxide absorber 6 containing soda lime granules removes carbon dioxide from the gas before it is breathed on the next cycle. The cycling of the ventilator machine is timed so that it has by now switched to vent to atmosphere—i.e it is in the expiratory phase of the ventilatory cycle.

Over successive cycles oxygen is taken up by the patient such that the bag 3 reduces in filled volume progressively with each cycle. As a result the bag 3 ultimately collapses to a point at which the pressure in the chamber 2 is greater than in the bag 3 and the chamber 5 above the valve disc 4. This causes the valve disc 4 to open by moving out of contact with the valve seat 8. As a result oxygen is able to flow via the conduit 9 and open oxygen substitution valve 4 into the chamber 5 and breathing system. The volume of oxygen that flows is self regulated to balance up the pressures on either side of the valve and therefore limited to replace the volume of gases taken up by the patient during the previous breath cycle. In practice this volume is comprised mainly of the oxygen uptake of the patient.

FIG. 4 shows the apparatus in the expiration phase. During the expiration phase, as the gas flows from the lungs, the pressure above the one way disc valve 4 (in chamber 5) will be the same as (or very marginally higher than) the pressure below the one way disc valve 4 (in conduit 9). As a result the valve will not inadvertently open during the expiration phase.

Referring now to FIG. 5 in which the ventilation apparatus is shown part way through the inspiratory phase. In this phase the pressure pulse of the gas from the ventilator machine 1 into the chamber 2 pushes a volume of gas into the lungs representing the size of one breath.

Gas (oxygen) flows into the lower chamber 2 from the ventilator machine 1. The pressure in the lower chamber 2 at any moment is transmitted through the wall of the flexible bag 3 to the gas inside it so that theoretically the pressure of the gas in the bag 3 is exactly the same as the pressure in the lower chamber 2 outside the bag.

It follows that in theory the pressure in the upper chamber 5, in continuity with the gas in the bag 3 should therefore also be at the same pressure as the gas in the lower chamber outside the bag. It would therefore be expected that the pressures above and below the disc of the oxygen substitution disc-valve 4 should be equal during inspiration and so this disc-valve 4 should not inadvertently open at any time (so long as there is some gas in the bag) during this phase of the ventilation cycle. This would prevent accidentally adding oxygen to the upper chamber 5 during this phase of the cycle. It would be expected that this would remain true even if the disc valve is not spring loaded or otherwise biased to the closed position in engagement with the valve seat. The weight of the disc valve 8 (which is light) is sufficient to effectively ensure that where the pressures are equal above and below the disc valve 4, the disc valve remains seated on the valve seat 8.

However in reality, if gas is added quickly by the ventilator machine 1 to the lower chamber 2, it takes a moment for all the pressure to equalize and the valve disc 4 can momentarily open or "flutter" during this inspiratory phase. This is not desirable as too much oxygen can be added to the upper chamber 5 if this happens.

In accordance with the invention, a solution is to direct the gas entering the lower chamber 2 such that the pressure in the conduit 9 below the valve does not increase immediately or more preferably lowers at least momentarily. In the embodiment shown in FIGS. 4 to 6 this is achieved by means of directing the gas entering the lower chamber 2 from the ventilator through a "venturi tube" 21 as shown, which has an exit opening directing the gas flow away from the disc valve 4. A first effect of "aiming" this gas jet at the bag 3 (i.e. away from the valve 4), the pressure pulse in the lower chamber 2 tends to be more rapidly conveyed to the upper chamber 5 via the gas in the bag 3. A second effect is that by using a venturi type flow arrangement, the gas flow into the lower chamber 2 tries to entrain the gas surrounding it into the flow. This cases the pressure immediately below the disc valve 4 to become very slightly lower than the pressure above the disc valve 4. This holds the disc shut during this phase, even if it is not spring loaded, which achieves the desired effect.

Figure 7:
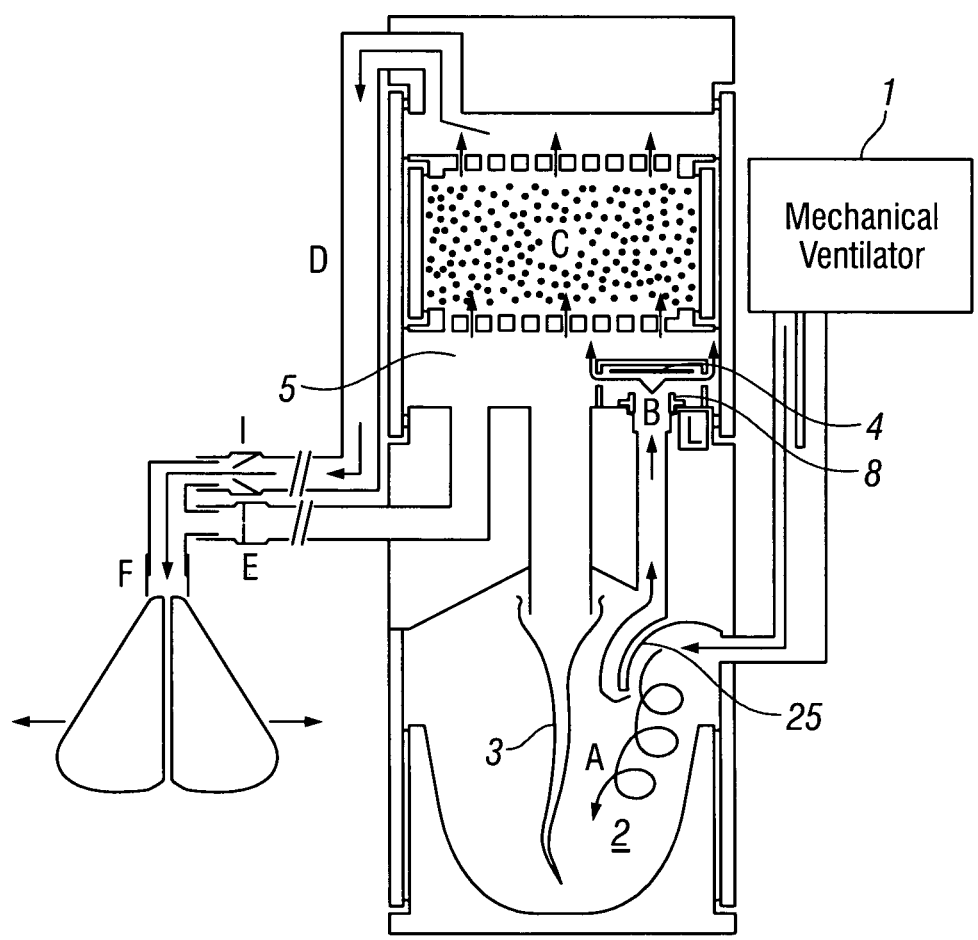
FIG. 7 is a schematic view of an alternative embodiment of ventilator apparatus.

A similar effect can be achieved in an alternative embodiment as shown in FIG. 7, in which a deflector baffle 25 is provided at the gas inlet into the lower chamber 2. The deflector baffle 25 is in the embodiment shown curved and integrally moulded with the chamber 2 wall. The technical effect of the baffle deflector has been found to provide similar results to the venturi type gas inlet described in the earlier embodiment, in that the pressure beneath the disc valve 4 reduces slightly as the gas delivered from the ventilator 1 enters the chamber 2. This small and temporary reduction in pressure is sufficient to prevent the unwanted addition of gas to the chamber 5 via the valve 4 at this part of the cycle. The flutter problem is therefore avoided.

At the end of the inspiratory phase, the bag 3 collapses fully as shown in FIG. 6. The reason for this is that during each inspiration/expiration cycle, the body of the patient consumes some oxygen metabolically via the lining of the lungs. The carbon dioxide produced by this metabolism is removed from the circulating gas by the soda-lime granules in the absorber canister 6. A sedated adult human might typically consume 250 ml/min of oxygen. Therefore if the ventilator is set to deliver 10 breaths per minute, then 25 ml of oxygen from the total gas volume will be removed from the system by the patient during each breath cycle. There may be additional uptake of other gases if present in the gas mixture, such as xenon, however this is very small relative to the oxygen uptake.

Therefore at end-expiration, the volume of gas in the bag will be approximately 25 ml less than the breath volume set on the mechanical ventilator to be delivered to the lower chamber 2. Therefore, near the end of the inspiratory cycle, the bag will collapse fully while the ventilator still has a small remaining volume of gas to add to the lower chamber. As the ventilator ads this last portion of the inspiratory gas to the lower chamber, the bag 3 can collapse no further and so this last quotient of the "driving gas" (i.e. oxygen from the mechanical ventilator) takes an "alternative" route and passes through the oxygen substitution disc valve 4 into the upper chamber 5, and the lungs continue to fill with gas until the inspiratory cycle is absolutely complete. The disc valve 4 opens at this time because this is the only situation when the pressure beneath the disc valve disc valve 4 exceeds the pressure above the disc valve 4. In FIG. 6 the valve is shown lifted from the valve seat 8 permitting the oxygen to pass directly into the upper chamber 5.

It must be remembered that the mechanical ventilator is ventilating the lower chamber 2 with pure oxygen. The overall effect of this is that at the end of each inspiration phase, a volume of oxygen is added to the circulating gas via the disc valve 4. The volume of oxygen added at steady state, assuming no leaks, is the same as the oxygen volume metabolically consumed by the patient during the previous breath cycle.

Therefore, the system is a closed re-breathing loop, but oxygen is automatically added to replace metabolic uptake by the patient. It should be appreciated that any other gases added to the recirculating gas cannot escape except by patient uptake. This makes for a potentially very cost-efficient anaesthetic agent delivery system for example. This is particularly the case where the anaesthetic agent is expensive such as for Xenon gas. The required volume of anaesthetic gas or mass of anaesthetic vapour may be added to the loop by an in feed line 24 for example as shown in FIG. 4, which is typically opened and closed by means of a suitable valve.

It should be noted that the walls of the bag chamber 2 are curved in a concave manner to provide a concave nest 2a for the bag 3 in its expanded configuration. A small spacing is provided between the nest 2a and the bag in its most expanded state (FIG. 4). Such a concaved nest or enclosure approximating to the shape of the bag in the expanded configuration has been found to provide improved performance because the 'dead volume' of the chamber 2 is minimised.

Alternative arrangements of ventilator apparatus may be used embodying the principle of the invention. Such an arrangement is shown in FIGS. 8 to 11 where as an alternative to the use of an inflatable bag, an exemplary system may use other means such as a collapsible bellows 503 type arrangement. The bellows 503 is positioned internally of the chamber 502 and is collapsed and expanded vertically during the breathing cycle. A disc valve 504 normally rests in a closed position on a valve seat 508 at the top of a conduit 509 communicating between the bellows chamber 502 and the closed loop breathing circuit The valve disc 504 is retained in a cage (not shown) which permits the valve to be lifted from seat 508 when the pressure differential above and below the valve disc 504 is sufficient. In such circumstances the disc valve 504 is caused to be raised to an open position permitting top up oxygen to be delivered to the closed loop system. The system loop includes a carbon dioxide absorber 506 containing soda lime granules. A communication conduit 511 delivers oxygen via a one way valve 512 to a patient breathing connection 513. A return conduit 514 communicates with the breathing connection 513 and communicates via a one way valve 515 and return conduit 516 with the interior of the collapsible bellows 503. The patient's lungs are shown schematically at 518.

The mechanical ventilator 501 machine pumps oxygen via the conduit 521 into the bellows chamber 502 to instigate the inspiration cycle. Conversely during the expiration phase, the oxygen in the chamber 502 vents to atmosphere via the ventilator machine 501.

In use, initially the system (which includes the interior of the bellows) is primed by filling with oxygen or an oxygen containing gas mixture. The breathing connection is connected to the patient (for example to an endotracheal tube positioned in the trachea of a patient) and secured. The mechanical ventilator 501 alternately pumps oxygen into the chamber 502 via the conduit 521, and then vents to atmosphere. Thus on each cycle, oxygen enters the chamber 502 via conduit 521 increasing the pressure in the chamber 502 and pressing in on the wall of the bellows 503 tending to collapse the bellows 503. The gas within the bellows 503 is accordingly driven into the closed loop breathing circuit towards the patient connector 513 via the conduit 511 and one way valve 512. The patient's lungs are then filled with oxygen causing them to expand. Exhaled gas containing carbon dioxide is then exhaled from the lungs 18 due to the passive recoil of the chest of the patient and these pass back into the circuit via the connector 13. The gases then pass via the one way valve 15 and conduit 16 into the interior of the bellows 503. The carbon dioxide absorber 506 containing soda lime granules removes carbon dioxide from the exhaled gas before it is breathed on the next cycle. The cycling of the ventilator machine is timed so that it has by now switched to the expiratory phase of the ventilatory cycle.

Figure 10:
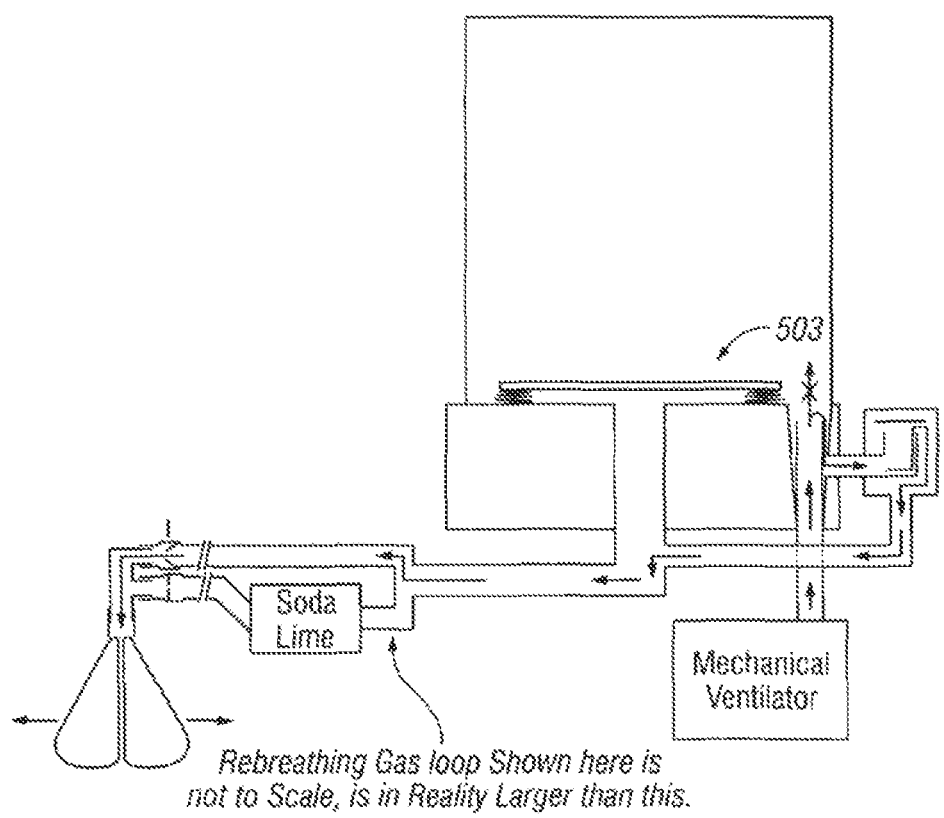

Over successive cycles oxygen is taken up by the patient such that the bellows 503 reduces in filled volume progressively with each cycle. As a result the bellows 3 ultimately collapses to a point (as shown in FIG. 100) at which the pressure in the chamber 502 is greater than in the bellows 503 and the chamber 505 above the valve disc 504. This causes the valve disc 504 to open by moving out of contact with the valve seat 508 (as shown in FIG. 10). As a result oxygen is able to flow via the conduit 509 and open oxygen substitution valve 504 into the chamber 505 and breathing system. The volume of oxygen that flows is self regulated to balance up the pressures on either side of the valve and therefore limited to replace the volume of gas, primarily oxygen, taken up by the patient in the previous breath cycle.

Figure 8:
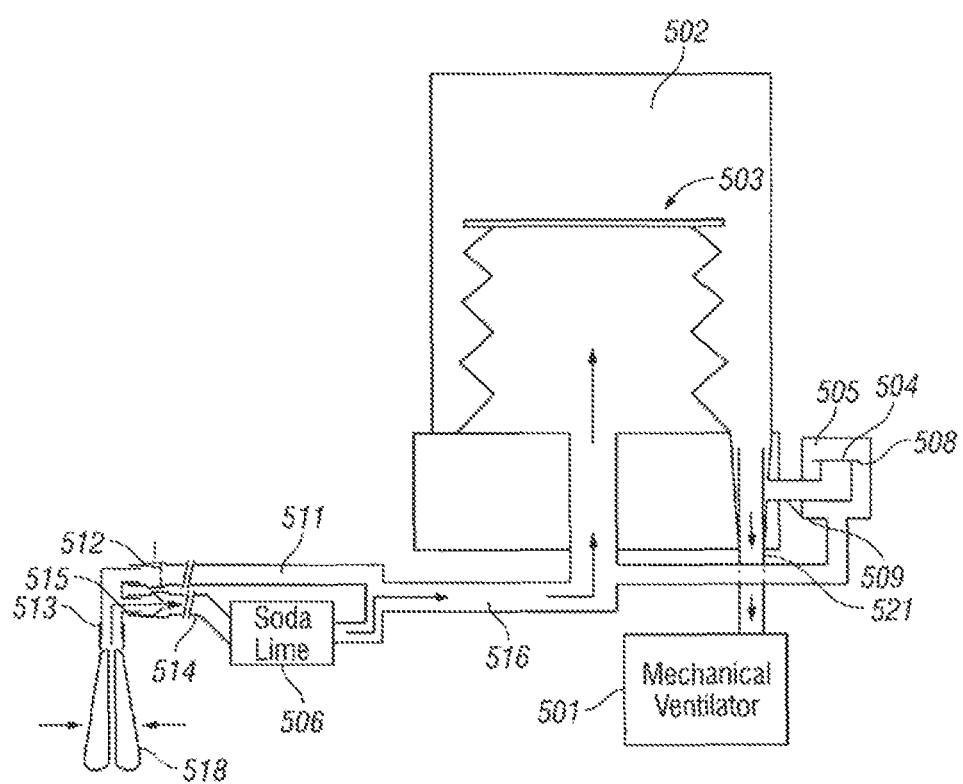
FIGS. 8 to 10 are views of a further alternative embodiment of ventilator apparatus at differing points in the breathing cycle.
Figure 9:
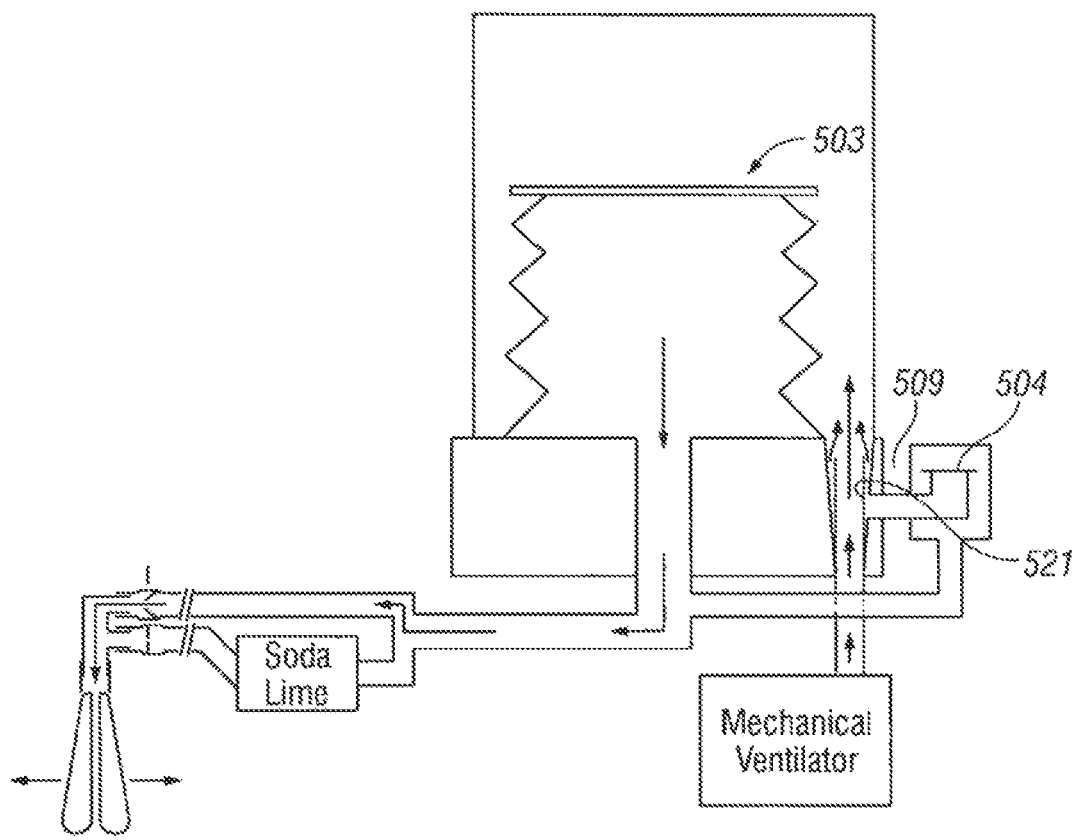

The operation in this embodiment is generally, similar to the earlier described embodiment. FIG. 8 shows the configuration during the expiratory phase. FIG. 9 shows the configuration part way through the inspiratory phase. FIG. 10 shows the system at the end of the inspiratory phase. In this embodiment, the flutter problem is avoided by means of the gas flow effect of the gas from the ventilator 501 along the conduit 521 directed into the interior of the chamber 502 past the open connection to the conduit 509 which leads to the valve. This direction of flow causes the reduced pressure or venture effect immediately below the disc valve 504 in a similar manner to that described in relation to the earlier embodiment. A true venturi effect may be created as shown in FIG. 9. The end of conduit 521 may be positioned beyond the connection to conduit 509 and a flow path in communication with conduit 509 may be defined externally of conduit 521. This causes gas flowing into the chamber 502 to entrain gas from the conical volume defined around the exterior of conduit 521, thereby causing the pressure reduction.

The invention claimed is:

1. Ventilator apparatus comprising:
a breathing circuit for supplying breathing gas to a patient, the breathing circuit including:
a variable volume enclosure provided within an enclosure chamber;
a gas supply path into the enclosure chamber being provided, permitting the enclosure chamber to be pressurized by the supplied gas in order to vary the volume of the variable volume enclosure; and
an alternative path for the gas supply being provided enabling the gas supplied, in predetermined circumstances, to enter directly into the breathing circuit via valve means;
wherein the gas supply path into the enclosure chamber is directed away from the valve means thereby reducing the enclosure chamber-side pressure at the valve means such that as a result of gas passing into the enclosure chamber the valve means is biased more firmly to a closed condition.

2. Ventilator apparatus according to claim 1, wherein the enclosure chamber-side pressure at the valve means becomes reduced slightly and with respect to the breathing circuit-side pressure.

3. Ventilator apparatus according to claim 1, wherein the effect to urge the valve means is more firmly to a closed condition is tailored to occur temporarily at the beginning of the inspiration phase of the breathing cycle.

4. Ventilator apparatus according to claim 1, wherein the gas supply is directed into the chamber away from a conduit connection to the valve means.

5. Ventilator apparatus according to claim 4, wherein a baffle or deflector is provided at the enclosure chamber to direct the supply gas away from the valve and/or toward the variable volume enclosure.

6. Ventilator apparatus according to claim 4, wherein a gas supply conduit has an outlet end communicating with the chamber, the gas supply conduit extending past conduit connection to the valve means.

7. Ventilator apparatus according to claim 1, wherein the valve means comprises a valve element arranged to rest on a valve seat in a valve closed configuration.

8. Ventilator apparatus according to claim 7, wherein the valve element is arranged to lift from the valve seat in the valve open configuration.

9. Ventilator apparatus according to claim 1, wherein the valve means is arranged to open when the variable volume enclosure is in a maximum collapsed state.

10. Ventilator apparatus according to claim 1, wherein the variable volume enclosure comprises a flexible bag or pouch.

11. Ventilator apparatus according to claim 1, wherein the variable volume enclosure comprises a collapsible bellows arrangement.

12. Ventilator apparatus according to claim 1, wherein the apparatus is used for delivering gas mixtures to a patient.

13. Ventilator apparatus according to claim 12, wherein the gas mixtures comprises respirable oxygen.

14. Ventilator apparatus according to claim 12, wherein the gas mixtures provide anesthesia to the patient.

15. Ventilator apparatus according to claim 12, wherein the gas mixtures provide at least one therapeutic treatment to the patient.

16. Ventilator apparatus according to claim 1, wherein the variable volume enclosure comprises a flexible bag or pouch and the wall of the enclosure chamber includes a concave form surface arranged to nest or cradle adjacent portions of the flexible bag or pouch in its expanded state.

* * * * *